US00PP12502P2

(12) United States Plant Patent
Cully

(10) Patent No.: US PP12,502 P2
(45) Date of Patent: Apr. 2, 2002

(54) BALD CYPRESS TREE NAMED 'NELSON'

(76) Inventor: Earl Cully, 846 Hoagland Rd., Box 84A, Jacksonville, IL (US) 62650

( * ) Notice: Subject to any disclaimer, the term of this patent is extended or adjusted under 35 U.S.C. 154(b) by 0 days.

(21) Appl. No.: 09/305,822

(22) Filed: Feb. 19, 1999

(51) Int. Cl.[7] ..... A01H 7/00

(52) U.S. Cl. ..... Plt./213

(58) Field of Search ..... Plt./213

(56) References Cited

U.S. PATENT DOCUMENTS

PP3,547 P * 5/1974 Cully ..... Plt./213
PP3,551 P * 5/1974 Cully ..... Plt./213

* cited by examiner

*Primary Examiner*—Bruce R. Campell
*Assistant Examiner*—Wendy C Baker

(57) ABSTRACT

A new and distinct bald cypress tree named 'Nelson' characterized by its distinct broad pyramidal habit of growth, beautiful dark green foliage, high resistance to insect pests, cold hardiness, the ability to resist breakage from wind and ice, and its rapid growth.

3 Drawing Sheets

The present invention comprises a new and distinct cultivar of bald cypress, botanically known as *Taxodium distichum*, and referred to by the cultivar name 'Nelson' (FIG. 1).

The initially discovered tree is growing in a cultivated tree evaluation area and arboretum owned by inventor Earl Cully, 846 Hoagland Road, eight miles southeast of Jacksonville, Ill., in Morgan County, in Township 14, Range 10.

The new cypress cultivar now named 'Nelson' is the result of a selection made from a population of approximately 20,000 seedlings grown from seed collected in southern Illinois and planted in the spring of 1975. Near the end of the first growing season, this four-month-old seedling tree stood out from all of the others in the seed bed. It had grown much taller, had a darker green foliage and had developed side branches that grew at a wide angle from the trunk. It was so superior that one could not help but notice its outstanding qualities, and thus it was transplanted to a cultivated area where it could be further evaluated.

This new cultivar 'Nelson' has been evaluated since the late summer of 1975. During that time span, it has continued to exhibit those same outstanding qualities that it displayed as a four-month-old seedling, namely rapid growth, dark green foliage, and a wide angle of branching. It has also proven to be extremely winter hardy, withstanding winter temperature lows of −28° F. without damage. It is highly resistant to wind and ice. It is also highly resistant to cypress twig gall and the Eriophyid mite. Because of its resistance to these two insect pests, it will hold a vibrant green foliage well into the autumn when it turns a beautiful bronze fall color. The wide angle habit of branching the tree exhibited as a seedling has continued, and today this broadly pyramidal tree (FIG. 2) has a limb spread of thirty-six feet, with a height of forty-five feet and a trunk diameter of 21 inches DBH (diameter at breast height 54" above ground level).

The 'Nelson' cultivar will make a great addition to the palette of good shade trees for city and residential planting in a large area of the United States. Its ability to grow in poorly drained soil, take intense summer heat, and tolerate little or no soil oxygen with pavement up to its trunk, make it an excellent choice for city planting. It will also be a good choice for park and lawn planting where space will allow.

The following characteristics in combination distinguish the new cultivar named 'Nelson' from other cultivars of

*Taxodium distichum*. To the knowledge of this inventor, the only two cultivars of *Taxodium distichum* introduced in this country were introduced by me in the early 1970's. They were the 'Monarch of Illinois' and the 'Shawnee Brave.' The 'Monarch of Illinois' is a broad spreading bald cypress, lacking apical dominance. It readily forks into two or three main trunks at four to ten feet above the ground. These forked central leaders usually share apical dominance. Branches of this tree tended to curve upward. The overall shape of the tree is broadly rounded in form. The 'Monarch of Illinois' is far less hardy than the 'Nelson.' It will survive as far north as Peoria, Ill., but has been killed in the Chicago area by winter cold.

The 'Shawnee Brave' differs from the 'Nelson' cultivar in form. The parent tree and all trees that have been asexually propagated from that parent tree have maintained this narrow form. It has a height of seventy feet with a total limb spread of eighteen feet.

1. The 'Nelson' cultivar is extremely cold hardy. It has withstood winter temperature lows of −28° F. with no damage. In the spring following those cold temperatures, the tree came into leaf and made normal growth during the summer season. During the severe winter of 1977–1978, the 'Nelson' cultivar was given a rigorous test for cold hardiness. At that time, the tree was only two years old and would have been at its most vulnerable to low temperature damage. However, it showed no damage after temperatures were −20° F. for long periods of time, with wind chills recorded at −80° F. In October 1991, the temperature was warm for the entire month without any frost to harden plants. On the last day of the month, the temperature dropped into the 'teens. Three days later on November 3, the temperature dropped to −1° F. This blast of arctic air killed young green ash and other deciduous tree species considered to be very hardy, and badly damaged many older trees. The 'Nelson' cultivar did not suffer the slightest damage from this unusual blast of arctic air. Based on its ability to survive these extreme winter lows, it would appear that the 'Nelson' cultivar would be reliably hardy in Zone 5A and the lower one-half of Zone 4B (USDA Plant Hardiness Zone Map).

2. The 'Nelson' cultivar is highly resistant to wind and ice. In the years that it has been under test it has suffered only minor damage from wind and no damage from ice. In a violent thunderstorm in the summer of 1993, when wind gusts were recorded at 80 mph, only one small limb was broken.

3. The 'Nelson' cultivar has strong apical dominance, and grows with a straight central leader with a wide angle habit of branching. It is a vigorous grower! Growth rate is approximately one-third more rapid than the species. Asexually propagated trees will make 3 to 4 feet and 4 to 5 feet of growth the first growing season.

4. The 'Nelson' cultivar is highly resistant to the cypress twig gall (*Cecidomyia cupressi*) and the Eriophyid mite. With the high resistance to the Eriophyid mite, the 'Nelson' bald cypress will hold vibrant green foliage until autumn when it turns a beautiful bronze fall color.

5. The foliage color is darker green than the species (FIG. 3).

PROPAGATION

Asexual propagation is done by bud grafting (chip budding) onto one-year-old bald cypress seedlings. This method of propagation has given a 95% to 98% bud stand. Propagation is being done near Jacksonville, Ill., and Aurora, Oreg. Asexual propagation by this method has proven to be very consistent and effective.

DETAILED BOTANICAL DESCRIPTION

In the following description, color references are made to The Royal Horticultural Society Colour Chart. The taxonomic description has been prepared by Thomas L. Green, Ph.D., Urban Forestry Professor, Western Illinois University, Macomb, Ill. 61455.

BRIEF DESCRIPTION OF THE DRAWINGS

The accompanying photographs illustrate the appearance and color of the new bald cypress tree, showing the colors as accurately as is reasonably possible to obtain in colored reproductions of this type. Actual foliage colors may differ slightly due to light reflection.

THE PLANT

Figure 1:
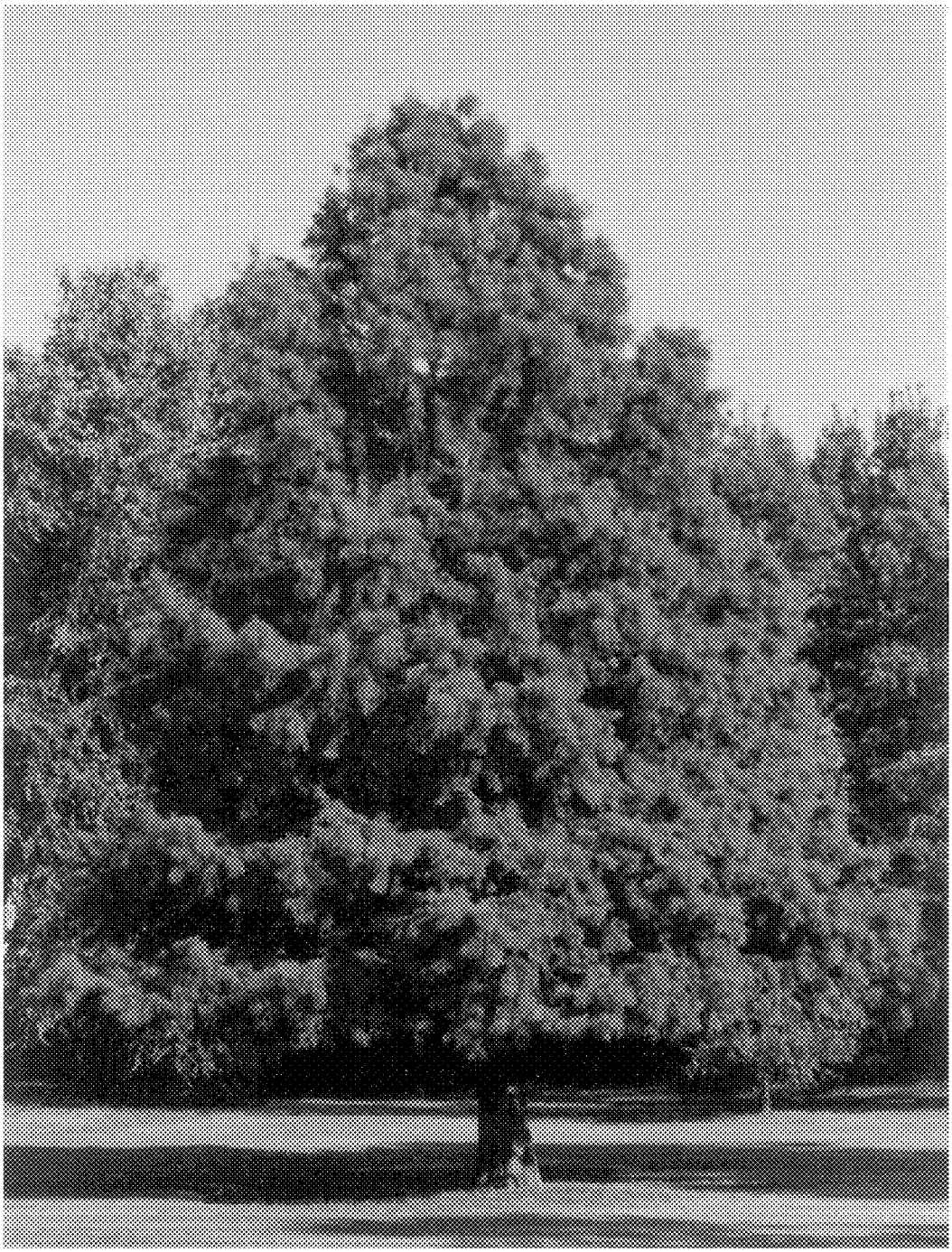
FIG. 1—depicts the initially discovered tree named 'Nelson'.
Figure 2:
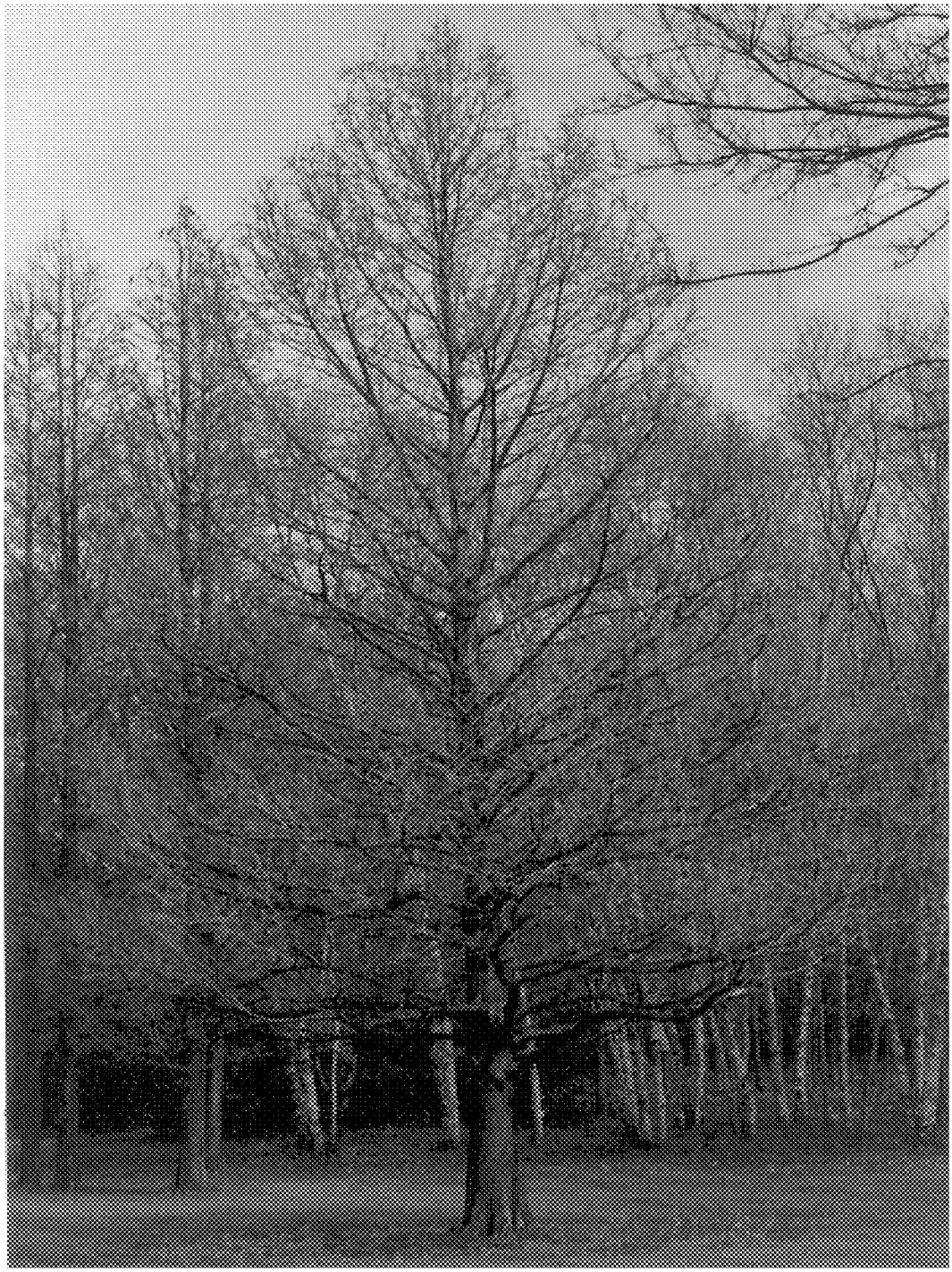
FIG. 2—depicts the 'Nelson' cultivar in early spring before the leaves appear, showing the wide angle habit of branching.
Figure 3:
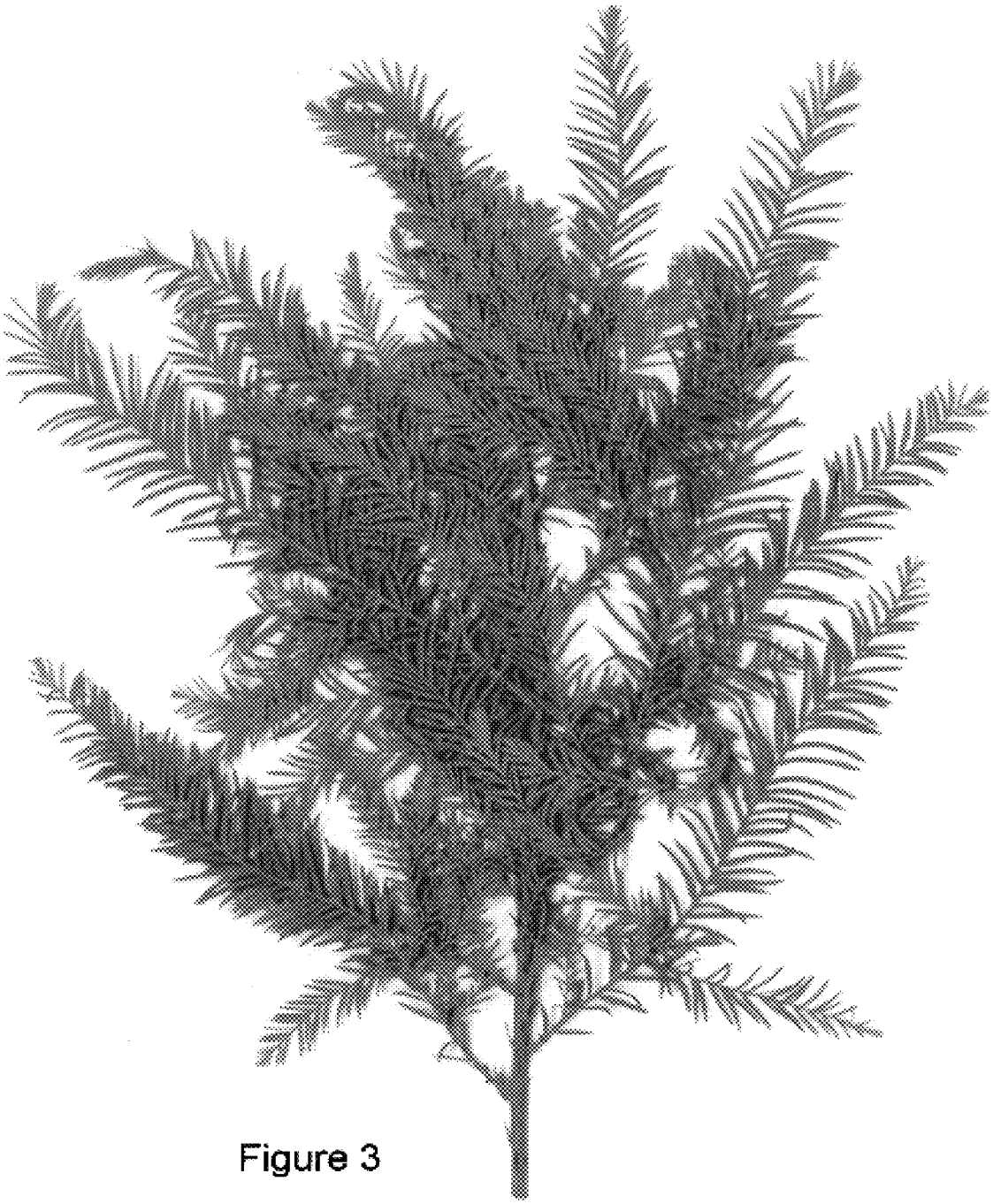
FIG. 3—depicts the color of the foliage, ranging through various shades of green (137A, 137B, 139B, and 139C).

Form: Tree.
Shape: Excurrent, broadly pyramidal.
Height: 13.7 m (45').
Spread: 11.0 m (36') at twenty-four years of age.
Trunk size: (dbh): 53.3 cm (21") 54" above grade level.
Strength: Excellent.
Bark (trunk): Bark light brown to gray green, long vertical furrows, peeling into strips (199C, 197A, 197B, 197C, 197D).
Branches:
- *Angle of attachment.*—On bottom portion of tree, branch angles 10°–30°; on top portion of tree, branch angles 45°–60°.
- *Spacing.*—Dense.

Leaves:
- *Length.*—10–18 mm; dense; borne singly in two rows on slender gray-brown twigs; flat, soft, flexible, featherlike.
- *Width.*—1–1.5 mm; taper to a point.
- *Form.*—Linear.
- *Margin.*—Entire.
- *Texture.*—Smooth, glabrous.
- *Quantity.*—Abundant.
- *Color.*—Upper side: green (137A, 137B, 139B and 139C). Lower side: Green (139D).
- *Thorns.*—None.
- *Spines.*—None.
- *Prickles.*—None.

Cones: Mature ovulate cones nearly globose, 2–2.5 cm in diameter, woody.
Seed: Not applicable.
Pollen: Not applicable.

OTHER DISTINGUISHING FEATURES/ ADVANTAGES

This tree is considered to be more vigorous than the species. It has excellent foliage quality and color, and a wide branch angle, giving it a broad pyramidal habit. It has also proven to be very winter hardy, withstanding −28° F. without damage, and resilient, with no breakage from wind, snow or ice. It has high resistance to the cypress twig gall (*Cecidomyia cupressi*) and the Eriophyid mite. This tree displays a beautiful bronze autumn color.

It is claimed:

1. A new and distinct cultivar of Bald Cypress *Taxodium distichum* plant named 'Nelson' as illustrated and described.

* * * * *